(12) United States Patent
Yoshida et al.

(10) Patent No.: US 10,288,574 B2
(45) Date of Patent: May 14, 2019

(54) WETTING SENSOR AND WETTING SENSING SYSTEM

(71) Applicant: NIPPON MEKTRON, LTD., Tokyo (JP)

(72) Inventors: Akio Yoshida, Tokyo (JP); Hiroyasu Hasegawa, Tokyo (JP)

(73) Assignee: NIPPON MEKTRON, LTD., Tokyo (JP)

(*) Notice: Subject to any disclaimer, the term of this patent is extended or adjusted under 35 U.S.C. 154(b) by 0 days.

(21) Appl. No.: 16/050,448

(22) Filed: Jul. 31, 2018

(65) Prior Publication Data

US 2019/0072508 A1 Mar. 7, 2019

(30) Foreign Application Priority Data

Sep. 6, 2017 (JP) ................................. 2017-171397

(51) Int. Cl.
*G01N 27/04* (2006.01)
*A61F 5/48* (2006.01)
*A61B 5/04* (2006.01)

(52) U.S. Cl.
CPC ............... *G01N 27/04* (2013.01); *A61B 5/04* (2013.01); *A61F 5/48* (2013.01)

(58) Field of Classification Search
CPC ... G01N 27/04; A61B 5/04; A61F 5/48; A61F 13/42; A61F 13/49004; A61F 13/2051; G08B 21/182; G08B 21/20
See application file for complete search history.

(56) References Cited

U.S. PATENT DOCUMENTS

| 9,314,381 | B2* | 4/2016 | Curran | A61F 13/42 604/361 |
|---|---|---|---|---|
| 2009/0292265 | A1* | 11/2009 | Helmer | A61F 13/42 604/361 |
| 2013/0036802 | A1* | 2/2013 | Johnson | G01N 27/223 73/74 |
| 2013/0324955 | A1* | 12/2013 | Wong | G01N 27/223 604/361 |
| 2014/0121473 | A1* | 5/2014 | Banet | A61B 5/6808 600/301 |
| 2014/0200538 | A1* | 7/2014 | Euliano | A61F 13/42 604/361 |

(Continued)

FOREIGN PATENT DOCUMENTS

| JP | 2009-210533 A | 9/2009 |
| JP | 2015-119784 A | 7/2015 |

*Primary Examiner* — An T Nguyen
(74) *Attorney, Agent, or Firm* — Studebaker & Brackett PC (57) ABSTRACT

A wetting sensor includes a stretchable circuit board having stretchability, a first stretchable wiring line as a wiring line formed on a main surface of the stretchable circuit board and having stretchability on the main surface, a second stretchable wiring line as a wiring line formed on the main surface of the stretchable circuit board and having stretchability on the main surface, a first electrode connected to the first stretchable wiring line, a second electrode connected to the second stretchable wiring line, a water absorbing member configured to cover at least a part of each of the first electrode and the second electrode, and a measurer configured to measure an electric characteristic between the first electrode and the second electrode which are contacting the water absorbing member.

8 Claims, 7 Drawing Sheets

(56) References Cited

U.S. PATENT DOCUMENTS

| | | | |
|---|---|---|---|
| 2014/0296808 A1* | 10/2014 | Curran | A61F 13/42 |
| | | | 604/361 |
| 2016/0051417 A1* | 2/2016 | Chiu | A61F 13/42 |
| | | | 604/361 |
| 2016/0250081 A1* | 9/2016 | Pugh | G08B 21/245 |
| | | | 604/361 |
| 2017/0258643 A1* | 9/2017 | Xu | A61F 13/42 |
| 2017/0354374 A1* | 12/2017 | Pepin | A61B 5/0002 |
| 2017/0354546 A1* | 12/2017 | Krasnow | A61F 13/42 |
| 2018/0036180 A1* | 2/2018 | Long | G06K 9/00771 |
| 2018/0116879 A1* | 5/2018 | Williams | A61F 13/42 |
| 2019/0072508 A1* | 3/2019 | Yoshida | G01N 27/04 |

\* cited by examiner

WETTING SENSOR AND WETTING SENSING SYSTEM

CROSS-REFERENCE TO RELATED APPLICATION

This application claims priority from Japanese Patent Application No. 2017-171397 filed with the Japan Patent Office on Sep. 6, 2017, the entire content of which is hereby incorporated by reference.

BACKGROUND

1. Technical Field

The present disclosure relates to a wetting sensor and a wetting sensing system.

2. Description of the Related Art

An adult care diaper is preferably replaced as soon as feces or urine is excreted. However, among care receivers receiving the care, some cannot inform others of the excretion immediately. Due to contact of excrement with the skin over a long period of time, skin inflammation of the care receiver might occur. For solving this problem, a wetting sensor configured to detect wetness of a diaper and a wetting sensing system using such a wetting sensor have been currently developed.

An example of a well-known wetting sensor is described in JP-A-2009-210533 and JP-A-2015-119784. An excretion detecting sensor described in JP-A-2009-210533 is used with the excretion detecting sensor being attached to, e.g., a disposable paper diaper. However, JP-A-2009-210533 fails to describe a substrate of the excretion detecting sensor or wiring line stretching according to motion of the paper diaper. According to the disposable diaper described in JP-A-2009-210533, the excretion detecting sensor contacts a care receiver, and therefore, the care receiver might feel uncomfortable when wearing the paper diaper.

Moreover, JP-A-2015-119784 describes a wearable article having a moisture sensor. According to the moisture sensor described in JP-A-2015-119784, ink is applied to a separate sheet provided between a disposable diaper and an incontinence pad, and in this manner, an electrode of the moisture sensor is formed. According to the wearable article described in JP-A-2015-119784, the electrode is provided on the outside of the disposable diaper, and therefore, does not influence a feeling of wearing of the disposable diaper.

SUMMARY

A wetting sensor includes a stretchable circuit board having stretchability, a first stretchable wiring line as a wiring line formed on a main surface of the stretchable circuit board and having stretchability on the main surface, a second stretchable wiring line as a wiring line formed on the main surface of the stretchable circuit board and having stretchability on the main surface, a first electrode connected to the first stretchable wiring line, a second electrode connected to the second stretchable wiring line, a water absorbing member configured to cover at least a part of each of the first electrode and the second electrode, and a measurer configured to measure an electric characteristic between the first electrode and the second electrode which are contacting the water absorbing member.

DESCRIPTION OF THE EMBODIMENTS

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

According to the wearing article according to JP-A-2015-119784, the electrode is provided on the outside of the disposable diaper via a liquid impermeable resin film. Thus, an electrode sheet having the electrode is less likely to get wet with body fluid, and therefore, can be reused. However, after excrement in the disposable diaper has been disposed, the electrode sheet needs to be placed on another disposable diaper. This provides a great burden on a caregiver.

Moreover, the electrode sheet does not stretch to specifically follow motion of the care receiver. For this reason, a wet portion of the disposable diaper does not contact the electrode depending on motion of the care receiver. Thus, the electrode sheet has the following problems, for example. Excretion cannot be sometimes detected. Alternatively, erroneous detection might occur when a part of the electrode sheet contacts other portions thereof due to, e.g., wrinkling or bending of the electrode sheet.

The present embodiment has been made in view of the above-described problems. The present embodiment relates to a wetting sensor provided inside a disposable diaper and a wetting sensing system using such a wetting sensor. The wetting sensor according to the present embodiment does not influence a feeling of wearing of a disposable diaper. The wetting sensor is suitably configured disposable. Further, the wetting sensor reduces occurrence of erroneous detection due to bending and the like.

A wetting sensor according to the present embodiment includes a stretchable circuit board having stretchability, a first stretchable wiring line as a wiring line formed on a main surface of the stretchable circuit board and having stretchability on the main surface, a second stretchable wiring line as a wiring line formed on the main surface of the stretchable circuit board and having stretchability on the main surface, a first electrode connected to the first stretchable wiring line, a second electrode connected to the second stretchable wiring line, a water absorbing member configured to cover at least a part of each of the first electrode and the second electrode, and a measurer configured to measure an electric characteristic between the first and second electrodes contacting the water absorbing member.

In the wetting sensor, the first electrode may include multiple first electrodes. The second electrode may be positioned between adjacent ones of the multiple first electrodes.

The first stretchable wiring line may have a first straight portion extending in one direction and a second straight portion extending parallel to the first straight portion. The first electrode may be formed raised in a direction opposite to a direction from the first straight portion toward the second straight portion or in a direction opposite to a direction from the second straight portion toward the first straight portion. The second stretchable wiring line may have a third straight portion extending parallel to the first straight portion and a fourth straight portion extending parallel to the second straight portion. The second electrode may include multiple second electrodes. Some of the second electrodes may be formed raised from the third straight portion toward the first straight portion and other of the second electrodes may be formed raised from the fourth straight portion toward the second straight portion.

The wetting sensor may further include a reference wiring line extending parallel to at least one of the first stretchable wiring line and the second stretchable wiring line. At least a part of the reference wiring line may have a stretch ratio equal to that of at least one of the first stretchable wiring line and the second stretchable wiring line.

The wetting sensor may further include a waterproof member configured to prevent or reduce contact between the reference wiring line and the water absorbing member.

In addition, a wetting sensing system according to the present embodiment includes the wetting sensor and a wetting determinator configured to determine a degree of water absorption of the water absorbing member based on the electric characteristic measured by the measurer of the wetting sensor.

The present embodiment can provide the wetting sensor provided inside the disposable diaper and the wetting sensing system using such a wetting sensor. The wetting sensor according to the present embodiment does not influence the feeling of wearing of the disposable diaper. The wetting sensor is suitably configured disposable. Further, the wetting sensor reduces occurrence of erroneous detection due to bending and the like.

Hereinafter, embodiments of the present disclosure will be described with reference to the drawings. Note that in all drawings, similar reference numerals are used to represent similar components. Further, overlapping description will be omitted as necessary. The drawings described below are schematic figures for describing each configuration illustrated in the drawing. Thus, the drawings are not intended to limit the embodiments of the present disclosure. The schematic figures illustrate, e.g., members included in the embodiments of the present disclosure and a relationship among the members. The drawings do not always illustrate precise shapes, sizes, lengths, heights, widths, and the like of the members included in the embodiments of the present disclosure.

First Embodiment

<Wetting Sensor>

Figure 1:
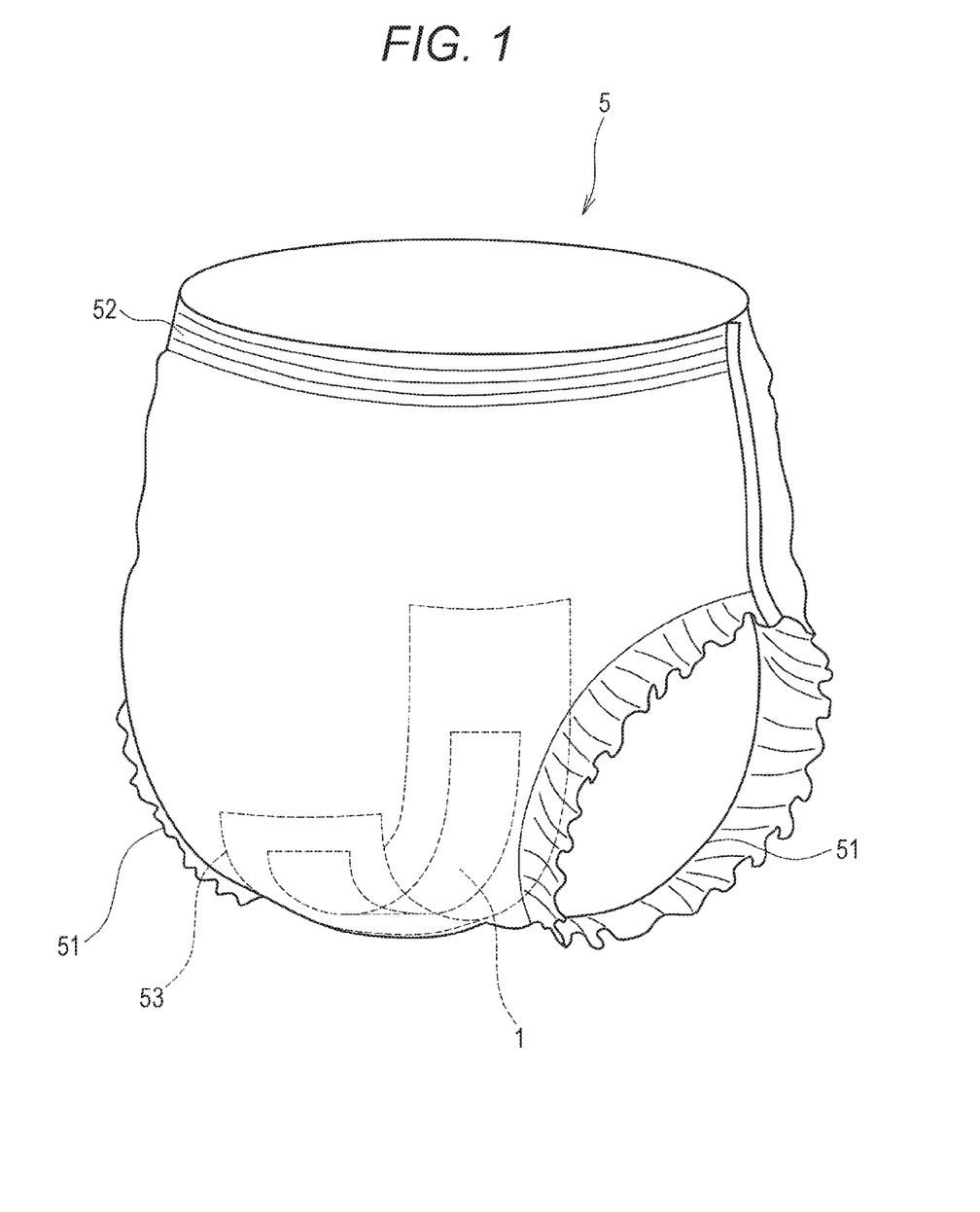
FIG. 1 is a view for describing a use example of a wetting sensor according to a first embodiment of the present disclosure.

FIG. 1 is a view for describing a use example of a wetting sensor according to a first embodiment. In the first embodiment, an example where the wetting sensor 1 is used being attached to a disposable diaper 5 will be described. The disposable diaper 5 is an underwear type diaper made of paper. Upon use of the disposable diaper 5, a body portion of a care receiver is fitted in a waist portion 52, and both legs protrude from leg portions 51. In the disposable diaper 5, a stretchable material is provided at the waist portion 52 and the leg portions 51. With this configuration, formation of a clearance between the disposable diaper 5 and the body of the care receiver is prevented or reduced.

The entirety of the disposable diaper 5 is formed by combination of paper members. The entirety of the disposable diaper 5 includes a surface material (an outer surface material) of an outermost portion, a surface material (an inner surface material) to be in contact with the skin surface of the care receiver, and a water absorbing material 53. The water absorbing material 53 is provided between the outer surface material and the inner surface material. Moreover, a waterproof material is provided between the water absorbing material 53 and the outer surface material. The water absorbing material 53 includes, for example, water absorbing paper, cotton-like pulp, and a water absorbing polymeric material. The wetting sensor 1 is attached to a surface of the water absorbing material 53 or the inside of the water absorbing material 53.

The water absorbing material 53 includes, for example, polyolefin non-woven fabric and a water absorbing polymeric material (macromolecular polymer) surrounded by cotton-like pulp. First, moisture having passed through the inner surface material spreads in the polyolefin non-woven fabric. Further, the moisture is sent to the cotton-like pulp and the water absorbing polymeric material. For example, polyolefin or polyester non-woven fabric is used as the outer surface material and the inner surface material. For example, a polyolefin film provided with fine pores for ensuring air permeability is used as the waterproof material.

Figure 2A:
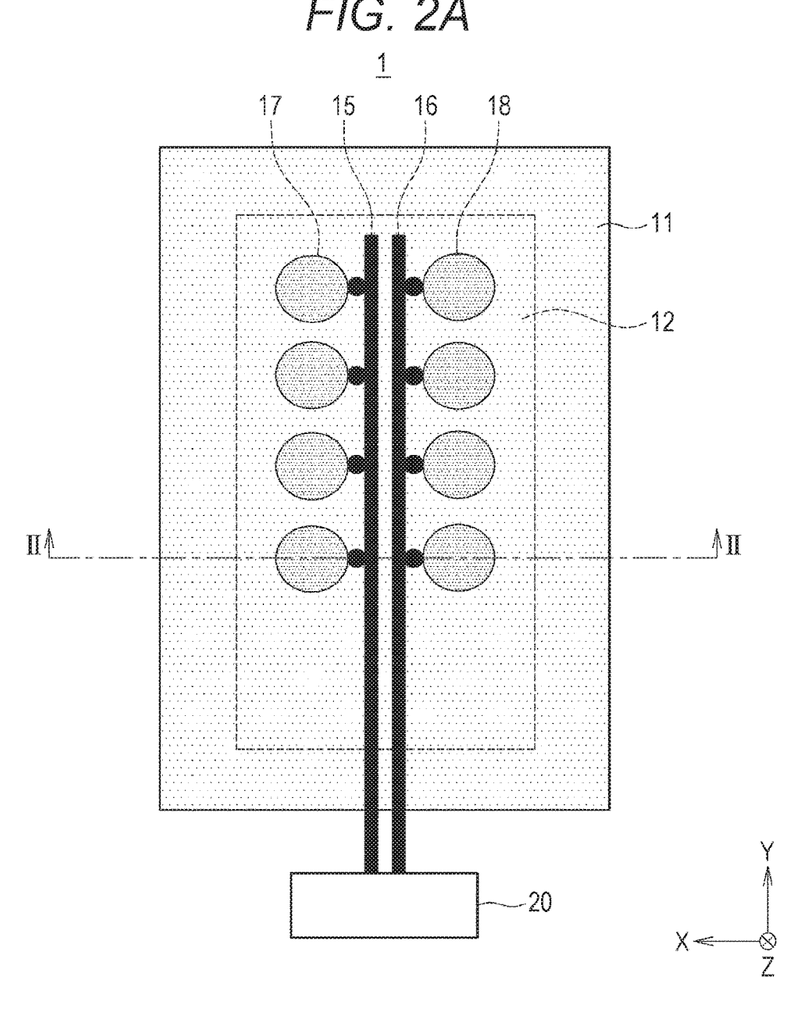
FIG. 2A is an upper view of the wetting sensor according to the first embodiment of the present disclosure.
Figure 2B:
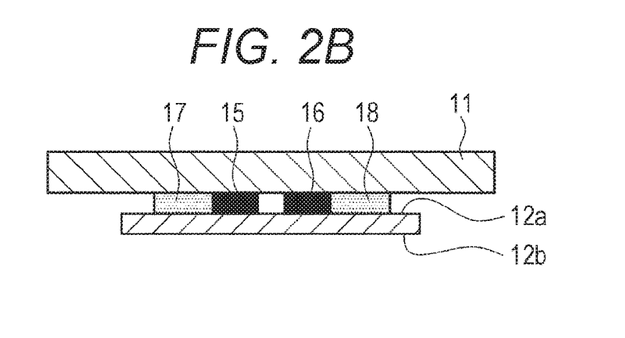
FIG. 2B is a sectional view of the wetting sensor according to the first embodiment of the present disclosure.

FIG. 2A is a view for describing the wetting sensor 1 according to the first embodiment, FIG. 2A illustrating an upper view of the wetting sensor 1. Note that the upper view described in the first embodiment is a view of the wetting sensor 1 viewed from the side of the inner surface material as described above. FIG. 2B is a sectional view of the wetting sensor 1 along an arrow II-II illustrated in FIG. 2A, FIG. 2B illustrating a view of a section of the wetting sensor 1 viewed from the direction of the arrow II-II. In FIG. 2A, a first stretchable wiring line 15, a second stretchable wiring line 16, first electrodes 17, and second electrodes 18 below the water absorbing material 11 are indicated by solid lines.

The wetting sensor 1 has a stretchable circuit board 12 having stretchability, the first stretchable wiring line 15, and the second stretchable wiring line 16. The first stretchable wiring line 15 and the second stretchable wiring line 16 are formed on a main surface 12a of main surfaces 12a, 12b of the stretchable circuit board 12. The first stretchable wiring line 15 and the second stretchable wiring line 16 have stretchability. In the first embodiment, the stretchability of each of the first stretchable wiring line 15 and the second stretchable wiring line 16 is constant across the main surface 12a. Note that the "main surface" means one(s) of surfaces of the stretchable circuit board 12 obviously having the largest area. In the present embodiment, a surface 14a and a surface 14b of the stretchable circuit board 12 are main surfaces.

Moreover, the wetting sensor 1 has the first electrodes 17 and the second electrodes 18. The first electrodes 17 are electrodes connected to the first stretchable wiring line 15. The second electrodes 18 are electrodes connected to the second stretchable wiring line 16.

Further, the wetting sensor 1 has the water absorbing material 11. The water absorbing material 11 covers at least a part of each of the first electrodes 17 and the second electrodes 18. The water absorbing material 11 is, together with the stretchable circuit board 12, the first stretchable wiring line 15, and the like, provided in the water absorbing material 53. In addition, the wetting sensor 1 has a measurer 20. The measurer 20 is configured to measure electric characteristics among the first electrodes 17 and the second electrodes 18, the first electrodes 17 and the second electrodes 18 contacting the water absorbing material 11.

"At least a part of each of the first electrodes 17 and the second electrodes 18" means a combination of at least some of the multiple first electrodes 17 and at least some of the multiple second electrodes 18. "At least a part of the first electrodes 17 and the second electrodes 18" may be all of the first electrodes 17 and the second electrodes 18. Moreover, "contacting the water absorbing material 11" may include not only "direct contact with the water absorbing material 11," but also "indirect contact through other layers or members."

Hereinafter, the above-described configuration will be described in sequence.

(Stretchable Circuit Board)

The stretchable circuit board 12 is a sheet-shaped member configured to stretch in at least one of in-plane directions. The stretchable circuit board 12 may preferably stretch in two of the in-plane directions. The stretchability of the stretchable circuit board 12 in the in-plane directions may exhibit isotropy or anisotropy. In a case where the stretchability of the stretchable circuit board 12 in the in-plane directions exhibits the anisotropy, the stretchability varies according to multiple directions in the plane of the stretchable circuit board 12. Preferably, a material contained in the stretchable circuit board 12 includes, but not limited to, elastomer materials such as nitrile rubber, latex rubber, urethane-based elastomer, and silicone-based elastomer. Specifically, even in a case where the wetting sensor 1 is attached to a human body skin with a urethane-based elastomer sheet for medical use, high safety can be obtained. The "sheet shape" described herein indicates a shape having a sufficiently-larger area as compared to a thickness. The thickness or area of the sheet is not specifically defined. The stretchable circuit board 12 may be formed of a single layer including a single sheet-shaped member. Alternatively, the stretchable circuit board 12 may be formed of multiple layers including multiple sheet-shaped stretchable circuit boards.

The thickness of the stretchable circuit board 12 is not specifically limited. Note that the thickness of the stretchable circuit board 12 is preferably equal to or less than 100 μm, from a viewpoint that stretching or motion of a target object (a target surface such as a living body surface) to which the stretchable circuit board 12 is attached is not inhibited. The thickness of the stretchable circuit board 12 is more preferably equal to or less than 25 μm, and much more preferably equal to or less than 10 μm.

As described above, according to the first embodiment, use of the thin sheet-shaped stretchable circuit board 12 having the stretchability does not inhibit motion of the care receiver. Thus, an uncomfortable feeling upon attachment can be sufficiently reduced. Moreover, the elastomer material exhibits air permeability. Thus, the uncomfortable feeling provided to the care receiver can be further reduced.

(First Stretchable Wiring Line, Second Stretchable Wiring Line)

The first stretchable wiring line 15 and the second stretchable wiring line 16 form a stretchable conductive pattern. In the first embodiment, the first stretchable wiring line 15 and the second stretchable wiring line 16 are formed on the outermost surface (or one main surface) of the single-layer stretchable circuit board 12. However, the first embodiment is not limited to such a configuration. In a case where the stretchable circuit board 12 is formed of the multiple layers, the first stretchable wiring line 15 and the second stretchable wiring line 16 may be formed on at least one main surface of the multiple stretchable circuit board layers included in the stretchable circuit board 12.

As illustrated in FIG. 2A, the first stretchable wiring line 15 extends in one direction. In the first embodiment, an extending direction is a Y-direction illustrated in FIG. 2A. The second stretchable wiring line 16 extends parallel to the first stretchable wiring line 15 (in the Y-direction).

The stretchability of each of the first stretchable wiring line 15 and the second stretchable wiring line 16 is constant across the main surface 12a. The constant stretchability described herein does not require a precise constant numeric value indicating the stretchability. The constant stretchability indicates that each of the first stretchable wiring line 15 and the second stretchable wiring line 16 on the main surface 12a does not locally include a portion with great stretchability or small stretchability, for example. Thus, in a case where the first stretchable wiring line 15 or the second stretchable wiring line 16 includes members with different levels of stretchability, the first stretchable wiring line 15 or the second stretchable wiring line 16 may be regarded as not having the constant stretchability. Examples of the first stretchable wiring line 15 and the second stretchable wiring line 16 with the constant stretchability include the first stretchable wiring line 15 and the second stretchable wiring line 16 simultaneously formed with the same material by the same technique.

The first stretchable wiring line 15 and the second stretchable wiring line 16 contain a conductive material. Thus, the first stretchable wiring line 15 and the second stretchable wiring line 16 exhibit conductivity. A material with favorable conductivity can be selected as the conductive material. The material with favorable conductivity includes, for example, silver, gold, platinum, carbon, copper, aluminum, cobalt, nickel, and alloy thereof. The shape of the conductive material is not specifically limited, but may be a particle form such as granulated powder or powder. The particle form is not specifically limited, but may be a spherical shape, a needle shape, a flake shape, a nanowire shape or the like. A particle aspect ratio may fall within a range of equal to or greater than 1 and equal to or less than 100, and specifically a range of equal to or greater than 1 and equal to or less than 50. The aspect ratio described herein means a ratio between the longest dimension and the shortest dimension of a three-dimensional body. When the aspect ratio of the particle contained in the first stretchable wiring line 15 and the second stretchable wiring line 16 falls within a range of equal to or greater than 5 and equal to or less than 20, a change in resistance when the stretchable circuit board 12 stretched in the in-plane directions deforms in a length direction can be reduced.

The first stretchable wiring line 15 and the second stretchable wiring line 16 preferably further contain a resin binder. That is, the first stretchable wiring line 15 and the second stretchable wiring line 16 according to the first embodiment are formed with the conductive material. The conductive material is obtained in such a manner that conductive particles are dispersed in a resin material while conductive resin is being mixed with the resin material. Since the first stretchable wiring line 15 and the second stretchable wiring line 16 contain the resin binder, rupturing of the first stretchable wiring line 15 and the second stretchable wiring line 16 due to stretching is reduced. The resin binder includes, but not limited to, a binder containing, as a main component, resin such as urethane or polyester, and a thermoplastic elastomer material such as silicone rubber, for example. Preferably, a resin binder with a low Young's modulus is selected such that the first stretchable wiring line 15 and the second stretchable wiring line 16 in the form of a coating have an elastic modulus equal to or less than that of the stretchable circuit board 12. A single type of elastomer material may be used. Alternatively, a mixture of multiple types of elastomer materials may be used.

The method for manufacturing the first stretchable wiring line 15 and the second stretchable wiring line 16 is not specifically limited. In the first embodiment, the first stretchable wiring line 15 and the second stretchable wiring line 16 are formed by a printing method. That is, the first stretchable wiring line 15 and the second stretchable wiring line 16 are printed patterns formed in such a manner that conductive paste having stretchability is printed and applied onto the main surface 12a of the stretchable circuit board 12. The printing method is not specifically limited. The printing method may include, a screen printing method, an inkjet printing method, a gravure printing method, an offset printing method and the like. Of these methods, screen printing is preferably used, considering fine resolution properties and film thickness stability. In the case of forming the first stretchable wiring line 15 and the second stretchable wiring line 16 by the printing method, conductive paste prepared to contain the above-described conductive particles, the above-described resin binder, and an organic solvent is preferably used. Stretchable conductive paste containing, as a main component, metal particles such as silver is used for the first stretchable wiring line 15 and the second stretchable wiring line 16, so that a stretch rate falling within a range of equal to or higher than about 50% and equal to or lower than about 70% can be realized, for example. Thus, a wiring line with excellent stretching properties can be formed.

The thickness and width dimensions of the first stretchable wiring line 15 and the second stretchable wiring line 16 can be determined based not only on resistivity under no load and a change in resistance upon stretching of the stretchable circuit board 12, but also on limitations of the thickness and width dimensions of the entirety of the stretchable circuit board 12. The width dimensions of the first stretchable wiring line 15 and the second stretchable wiring line 16 are preferably equal to or less than 1000 µm, more preferably equal to or less than 500 µm, and much more preferably equal to or less than 200 µm. The above-described width dimensions of the first stretchable wiring line 15 and the second stretchable wiring line 16 are based on the point of view that the first stretchable wiring line 15 and the second stretchable wiring line 16 follow a change in the dimensions upon stretching of the stretchable circuit board 12 to ensure favorable stretchability. The thickness dimensions of the first stretchable wiring line 15 and the second stretchable wiring line 16 may be equal to or less than 25 µm, and preferably fall within a range of equal to or greater than 10 µm and equal to or less than 15 µm.

(First Electrode, Second Electrode)

As described above, the first electrodes 17 are the electrodes connected to the first stretchable wiring line 15. The second electrodes 18 are the electrodes connected to the second stretchable wiring line 16. Each first electrode 17 is formed raised in the direction opposite to the direction from the first stretchable wiring line 15 toward the second stretchable wiring line 16. Moreover, each second electrode 18 is formed raised in the direction opposite to the direction from the second stretchable wiring line 16 toward the first stretchable wiring line 15. In the first embodiment, such directions of the first electrode 17 and the second electrode 18 will be hereinafter sometimes described as "raised outward."

The first electrodes 17 and the second electrodes 18 can be manufactured by a process similar to that for the first stretchable wiring line 15 and the second stretchable wiring line 16. For example, in a case where the first stretchable wiring line 15 and the second stretchable wiring line 16 are manufactured by silk screen printing, patterns of the first electrodes 17 and the second electrodes 18 are, together with patterns of the first stretchable wiring line 15 and the second stretchable wiring line 16, formed on a printing plate, and in this manner, all of the first stretchable wiring line 15, the second stretchable wiring line 16, the first electrodes 17, and the second electrodes 18 can be printed and formed at once. According to the first embodiment, the first electrodes 17 and the second electrodes 18 are manufactured at the same time as manufacturing of the first stretchable wiring line 15 and the second stretchable wiring line 16, and therefore, stretchability similar to that of the first stretchable wiring line 15 and the second stretchable wiring line 16 can be provided to the first electrodes 17 and the second electrodes 18. This process is preferred considering enhancement of a manufacturing efficiency.

(Measurer)

The measurer 20 measures the electric characteristics between the first stretchable wiring line 15 and the second stretchable wiring line 16, and output a measurement result. In the first embodiment, the measurer 20 measures an impedance between the first stretchable wiring line 15 and the second stretchable wiring line 16 while the impedance is used as the electric characteristics.

In the first embodiment, the measurer 20 includes a measurement device, a transmitter, and a power source. Any of the measurement device, the transmitter, and the power source is not shown in the figure. The measurement device is configured to measure the impedance. The transmitter is configured to transmit, to the outside, the value of the impedance measured by the measurement device. The power source is configured to supply power to the measurement device and the transmitter. The measurer 20 as described above is a well-known IC chip, and therefore, further description thereof will be omitted.

In the first embodiment, the measurer 20 may be formed on the stretchable circuit board 12. Alternatively, the measurer 20 may be provided separately from the stretchable circuit board 12, and may be used together with the stretchable circuit board 12. The measurer 20 may be the well-known IC chip as described above, or may be formed by a printing technique. The disposable diaper 5 is replaced two or three times a day. Thus, the measurer 20 preferably includes a compact measurement device with small power consumption. Further, the measurer 20 preferably includes a compact power source workable for around 10 hours and having a sufficient capacity to transmit a signal once.

Note that in the first embodiment, the electric characteristics as a measurement target are not limited to the impedance. Examples of conceivable other electric characteristics include the value of current flowing between the first stretchable wiring line 15 and the second stretchable wiring line 16, and a resistance value between the first stretchable wiring line 15 and the second stretchable wiring line 16.

(Water Absorbing Member)

The water absorbing material 11 covers at least a part of each of the first electrodes 17 and the second electrodes 18. According to the first embodiment, the water absorbing material 11 covers all of the first electrodes 17 and the second electrodes 18 as illustrated in FIG. 2A. Note that the first embodiment is not limited to such a configuration. Of the electrodes connected to the first stretchable wiring line 15 or the second stretchable wiring line 16, the electrodes used for a purpose different from measurement of the impedance are not covered in some cases.

The water absorbing material 11 according to the first embodiment is a water absorbing core obtained in such a manner that water absorptive polymer particles are held on a pulp fiber assembly. Note that the water absorbing material 11 according to the first embodiment is not limited to such a configuration. As long as the water absorbing material 11 has the function of absorbing the moisture having spread from the inside of the disposable diaper 5 and transmitting information on the absorbed moisture to the first electrodes 17 and the second electrodes 18, the water absorbing material 11 may have any configuration.

(Operation)

The care receiver wears the disposable diaper 5 to which the wetting sensor 1 is attached. In this state, when the care receiver excretes, moisture in excreted feces or urine reaches the water absorbing material 11 through an inner surface of the disposable diaper 5. The water absorbing material 11 absorbs the moisture in the excrement of the care receiver while being arranged closer to the care receiver than the first electrodes 17 and the second electrodes 18 are arranged. The moisture spreads across the water absorbing material 11 according to the amount of moisture, and is supplied to the first electrodes 17 and the second electrodes 18. Thus, in the wetting sensor 1, the area of the first electrodes 17 and the second electrodes 18 according to the amount of moisture in the excrement gets wet. Wetting of the first electrodes 17 and the second electrodes 18 change the impedance between the first stretchable wiring line 15 and the second stretchable wiring line 16. The amount of change in the impedance changes according to the wet area of the multiple first electrodes 17 and the multiple second electrodes 18. In the first embodiment, a larger wet area of the first electrodes 17 and the second electrodes 18 results in a lower impedance. Thus, according to the first embodiment, the impedance between the first stretchable wiring line 15 and the second stretchable wiring line 16 is measured, so that the degree of wetting of the water absorbing material 11 and therefore the degree of wetting of the surface (an arrangement surface) on which the first electrodes 17 and the second electrodes 18 are arranged can be detected.

Note that in the first embodiment, the first electrodes 17 and the second electrodes 18 are arranged in an X-direction (a right-to-left direction) in FIG. 2A. Thus, the wetting sensor 1 according to the first embodiment is specifically suitable for detecting the wet area spreading in a lateral direction.

<Wetting Sensing System>

Figure 3:
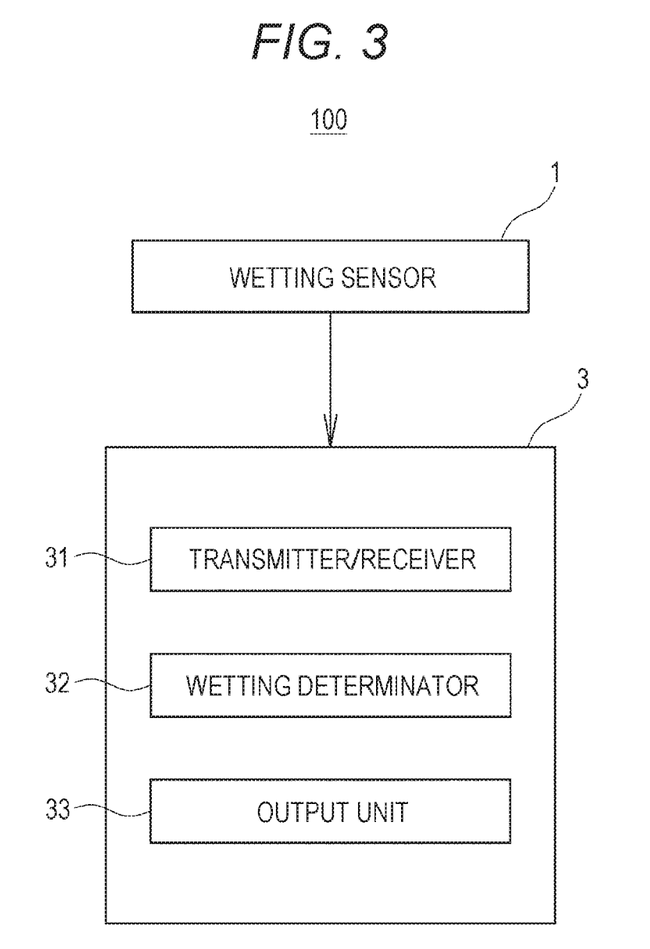
FIG. 3 is a functional block diagram for describing a wetting sensing system according to the first embodiment.

Next, a wetting sensing system using the wetting sensor 1 described above will be described. FIG. 3 is a functional block diagram for describing the wetting sensing system 100 according to the first embodiment. The wetting sensing system 100 according to the first embodiment includes the wetting sensor 1 and a wetting determinator 32. In the first embodiment, the wetting determinator 32 is provided in a well-known information processing device 3 such as a personal computer (PC) or a smartphone. In this case, the wetting determinator 32 includes a program operable in the information processing device 3, and hardware of a terminal device.

The impedance is the electric characteristic measured by the measurer 20 of the wetting sensor 1. The wetting determinator 32 is configured to determine the degree of water absorption of the water absorbing material 11 based on the impedance. That is, the measurer 20 of the wetting sensor 1 has a not-shown transmitter. The measurer 20 transmits, as a voltage value, the impedance obtained by measurement to the information processing device 3. The wetting determinator 32 of the information processing device 3 determines, from the transmitted voltage value, the degree of wetting of the water absorbing material 11. The transmitted voltage value is an impedance among the first electrodes 17 and the second electrodes 18. The impedance among the first electrodes 17 and the second electrodes 18 can be also considered as the impedance between the first stretchable wiring line 15 and the second stretchable wiring line 16. Determination on the degree of wetting is realized as follows, for example. The impedance obtained by measurement is compared with data provided in advance in the wetting determinator 32, the data indicating an association between the impedance and the degree of wetting. Further, the degree of wetting corresponding to the impedance obtained by measurement is selected. In this manner, the degree of wetting is determined. Alternatively, the wetting determinator 32 stores, in advance, a calculation expression for obtaining the degree of wetting with the impedance taken as a variable. Further, the impedance obtained by measurement is assigned to the calculation expression, and in this manner, the degree of wetting is calculated. In this manner, determination on the degree of wetting can be also realized. As described above, the wetting sensor 1 according to the first embodiment can not only detect excretion of the care receiver, but also can determine the degree of excretion.

The information processing device 3 including the built-in wetting determinator 32 has a transmitter/receiver 31 and an output unit 33. The transmitter/receiver 31 is configured to receive the voltage value as the impedance measured by the measurer 20. The information processing device 3 has the output unit 33 configured to output a determination result of the wetting determinator 32. The transmitter/receiver 31 includes existing hardware and software used for transmission/receiving in the information processing device 3. In this configuration, the transmitter/receiver 31 may use a communication function of the information processing device 3 for a connection with a network line. The output unit 33 may output the determination result by any of an image, a text, voice, buzzer, and the like. In the case of outputting the determination result as the image or the text, a program for image production, a display screen, and a driver thereof function as the output unit 33. In the case of outputting the determination result as the voice, existing voice synthesis program and speaker in the information processing device 3 function as the output unit. In the case of outputting the determination result as sound or light, existing sound generation program and speaker in the information processing device 3 function as the output unit 33.

In a case where a distance between the wetting sensor 1 and the information processing device 3 is relatively long and the distance goes beyond a transmittable range of a transmission function of the wetting sensor 1, the wetting sensing system 100 may include communication relay equipment at a bed of the care receiver or in a residential space of the care receiver. With this configuration, the transmitter of the wetting sensor 1 is good enough as long as the transmitter has the function of transmitting a signal to the relay equipment at a position relatively close to the care receiver. The relay equipment having a sufficient signal transmission function is configured to transmit, to the information processing device 3, a signal transmitted from the wetting sensor 1. In a case where the care receiver is housed at a medical facility and the like, the information processing device 3 may be a PC placed at a nurses' station and the like. Alternatively, the information processing device 3 may be a communication terminal owned by a caregiver, such as a smartphone. As another alternative, the information processing device 3 may be equipment dedicated for receiving and processing a detection signal of the wetting sensor 1.

Further, the information processing device 3 may have the function of recording the time of signal transmission from the wetting sensor 1. With this configuration, the wetting sensing system according to the first embodiment can record the time of excretion of the care receiver over a long period of time. Thus, the wetting sensing system according to the first embodiment can identify, for each care receiver, a time and timing with a high probability of excretion. The timing with a high probability of excretion is, for example, two hours after wake-up or within one hour after meals. The caregiver guides the care receiver to a restroom according to the timing of excretion for each care receiver, so that excretion of the care receiver can be efficiently supported.

According to the first embodiment described above, the stretchable circuit board 12 is used. Thus, the wetting sensor 1 stretches flexibly according to motion of the care receiver. Further, the measurer 20 provided at the wetting sensor 1 can be realized by a tiny IC chip. Thus, the wetting sensor 1 according to the first embodiment does not provide the uncomfortable feeling to the care receiver even when the wetting sensor 1 is attached to the inside of the disposable diaper 5. Moreover, the wetting sensor 1 is attached to the inside of the disposable diaper 5, and therefore, is preferably disposable together with the disposable diaper 5. Further, the wetting sensor 1 (a disposable sensor 1) having the stretchable circuit board 12 following motion of the care receiver is less wrinkled or bent in the disposable diaper 5. Thus, occurrence of erroneous detection due to contact between portions of the first stretchable wiring line 15, contact between portions of the second stretchable wiring line 16, or contact between the first stretchable wiring line 15 and the second stretchable wiring line 16 can be reduced.

The first stretchable wiring line 15 and the second stretchable wiring line 16 have the stretchability. Further, the first stretchable wiring line 15 and the second stretchable wiring line 16 have a uniform stretch ratio on the stretchable circuit board 12. Thus, the first stretchable wiring line 15 and the second stretchable wiring line 16 follow motion of the care receiver to stretch together with the stretchable circuit board 12, and are not locally ruptured or deformed. In addition, even upon stretching, the first stretchable wiring line 15 and the second stretchable wiring line 16 as described above can maintain stable electric characteristics.

Thus, the first embodiment can provide the wetting sensor provided inside the disposable diaper and the wetting sensing system using such a wetting sensor. The wetting sensor according to the first embodiment does not influence a feeling of wearing of the disposable diaper. The wetting sensor is suitably configured disposable. Further, the wetting sensor reduces occurrence of erroneous detection due to bending and the like.

Further, according to the first embodiment, the sheet-shaped stretchable circuit board 12 having the stretchability is used, so that a process management cost can be reduced as compared to the case of using, e.g., a well-known substrate exhibiting flexibility. That is, when the well-known flexible substrate is produced, a photofabrication step such as patterning or a curing step for cover laminate and the like is not necessary for the stretchable circuit board 12. Thus, according to the wetting sensor 1 of the first embodiment using the stretchable circuit board 12, a total process management cost can be reduced. Consequently, the unit price of the wetting sensor can be kept low. The wetting sensor 1 according to the first embodiment is more suitably configured disposable from the aspect of cost.

Second Embodiment

Figure 4A:
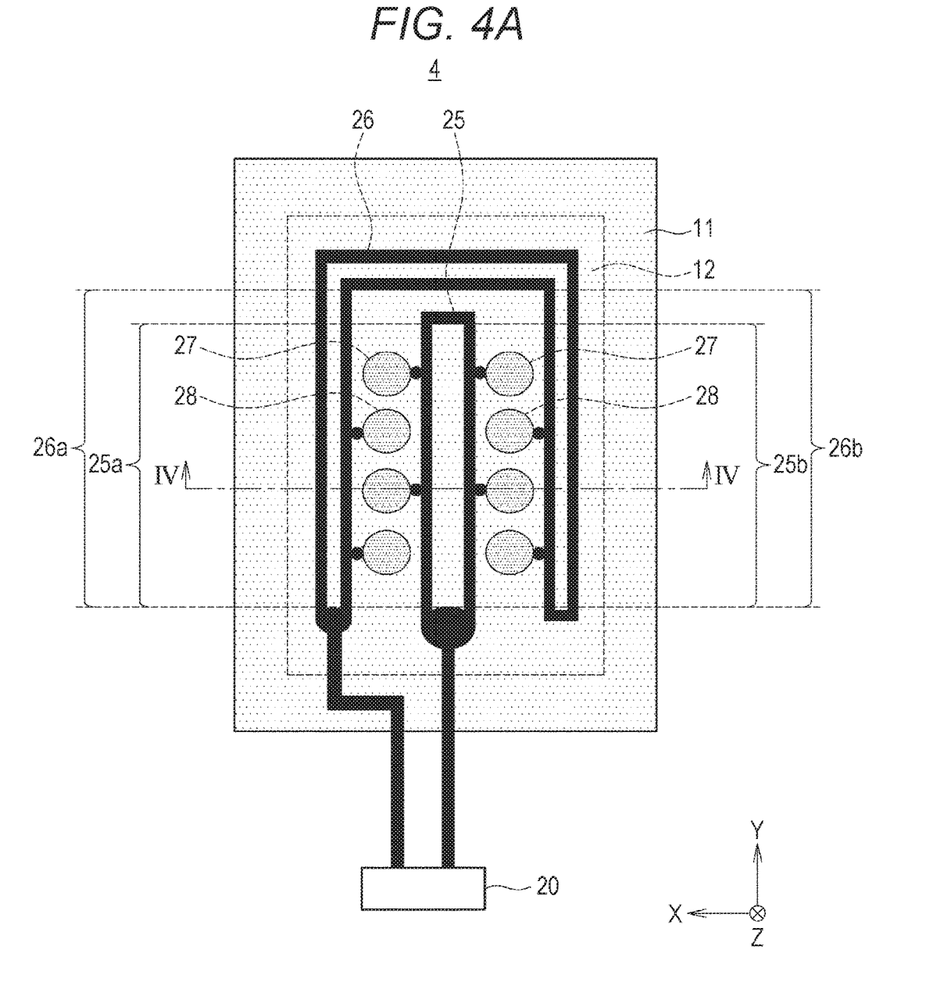
FIG. 4A is an upper view of a wetting sensor according to a second embodiment of the present disclosure.
Figure 4B:
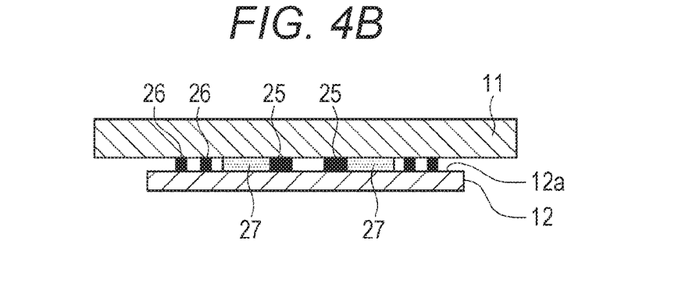
FIG. 4B is a sectional view of the wetting sensor according to the second embodiment of the present disclosure.

Next, a wetting sensor 4 according to a second embodiment of the present disclosure will be described. At the wetting sensor 4, electrodes are more densely arranged as compared to the electrodes of the wetting sensor 1 according to the first embodiment. The wetting sensor 4 is provided for the purpose of detecting a wet area of a water absorbing material 11 with high accuracy.

FIGS. 4A and 4B are views for describing the wetting sensor 4 according to the second embodiment. FIG. 4A is an upper view of the wetting sensor 4. FIG. 4B is a sectional view of the wetting sensor 4 along an arrow IV-IV in FIG. 4A, FIG. 4B illustrating a section of the wetting sensor 4 viewed from the direction of the arrow IV-IV. Note that in FIG. 4A, for the sake of convenience, a configuration below the water absorbing material 11 is indicated by a solid line.

The wetting sensor 4 has a first stretchable wiring line 25 and a second stretchable wiring line 26 formed on a stretchable circuit board 12, first electrodes 27 connected to the first stretchable wiring line 25, and second electrodes 28 connected to the second stretchable wiring line 26. The first electrodes 27 and the second electrodes 28 are covered with the water absorbing material 11. Further, the wetting sensor 4 according to the second embodiment has a measurer 20 configured to measure an impedance among the first electrodes 27 and the second electrodes 28.

As illustrated in FIG. 4A, the wetting sensor 4 has the multiple first electrodes 27 and the multiple second electrodes 28. At least one of the second electrodes 28 is arranged and positioned between adjacent ones of the first electrodes 27. With this configuration, the first stretchable wiring line 25 and the second stretchable wiring line 26 can be arranged closer to each other as compared to the first stretchable wiring line 15 and the second stretchable wiring line 16 in the wetting sensor 1. Thus, the wetting sensor 4 according to the second embodiment has wetting measurement points with density higher than that of the measurement points of the wetting sensor 1 according to the first embodiment. The wetting sensor 4 having the measurement points with high density can output multiple levels of the value of the impedance according to the degree of wetting. Thus, the wetting sensor 4 can determine the degree of wetting with high accuracy.

As illustrated in FIG. 4A, in the wetting sensor 4, the first stretchable wiring line 25 includes a first straight portion 25a extending in one direction, and a second straight portion 25b extending parallel to the first straight portion 25a. Each first electrode 27 is formed raised in the direction opposite to the direction from one of the first straight portion 25a and the second straight portion 25b toward the other one of the first straight portion 25a and the second straight portion 25b. It can be said that the first electrodes 27 are formed raised outward. Moreover, the second stretchable wiring line 26 includes a third straight portion 26a extending parallel to the first straight portion 25a, and a fourth straight portion 26b extending parallel to the second straight portion 25b. Some of the second electrodes 28 are formed raised from the third straight portion 26a toward the first straight portion 25a, and the remaining second electrodes 28 are formed raised from the fourth straight portion 26b toward the second straight portion 25b.

The phrasing of "the second electrodes 28 are formed raised from the third straight portion 26a toward the first straight portion 25a" as described herein indicates that the second electrodes 28 are connected to the third straight portion 26a while being positioned between the third straight portion 26a and the first straight portion 25a. The phrasing of "the second electrodes 28 are formed raised from the fourth straight portion 26b toward the second straight portion 25b" indicates that the second electrodes 28 are connected to the fourth straight portion 26b while being positioned between the fourth straight portion 26b and the second straight portion 25b.

According to the wetting sensor 4 of the second embodiment, the first electrodes 27 and the second electrodes 28 are arranged side-by-side in a Y-direction (an upper-to-lower direction) illustrated in FIG. 4A. Thus, the wetting sensor 4 according to the second embodiment is specifically suitable for detecting the wet area spreading in a longitudinal direction.

Figure 5A:
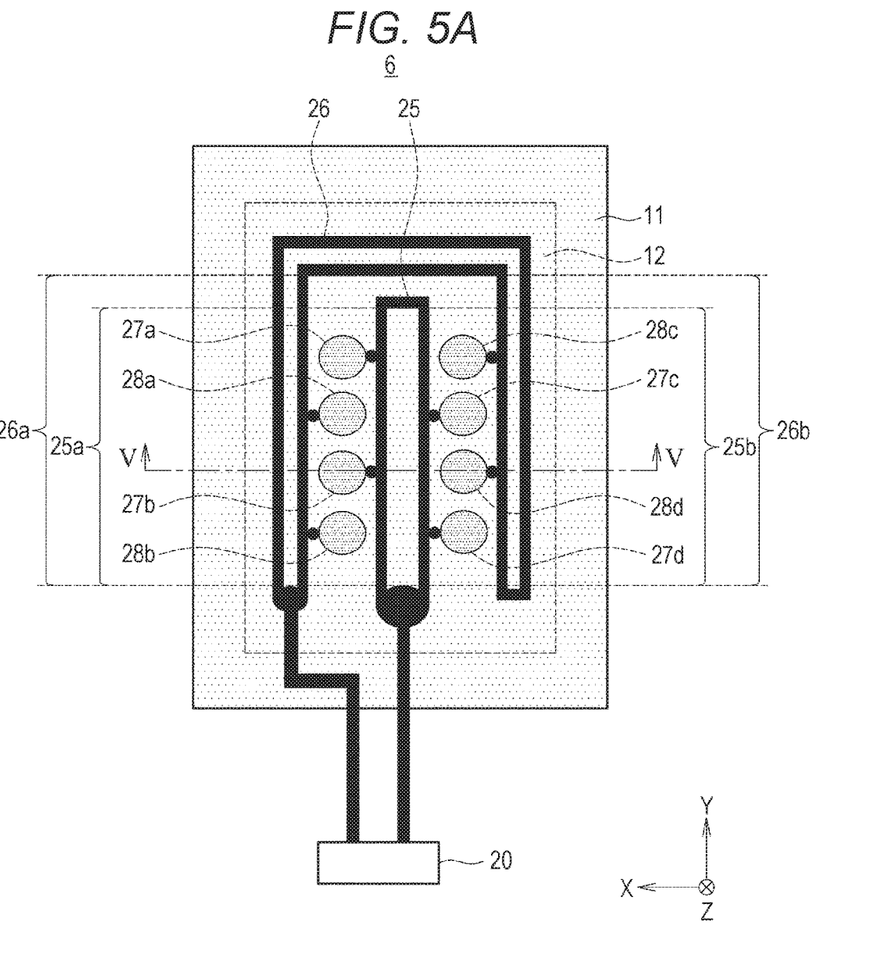
FIG. 5A is an upper view of a wetting sensor of a variation of the second embodiment of the present disclosure.
Figure 5B:
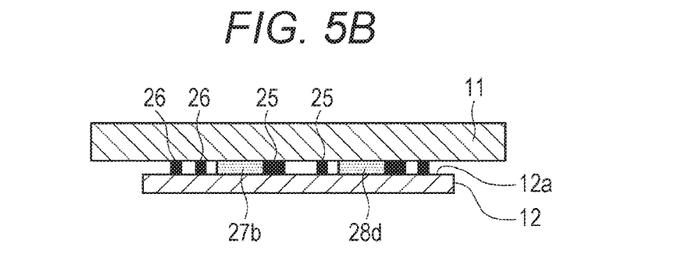
FIG. 5B is a sectional view of the wetting sensor of the variation of the second embodiment of the present disclosure.

The second embodiment is not limited to such a configuration. FIGS. 5A and 5B are views for describing a wetting sensor 6 of a variation of the second embodiment. FIG. 5A is an upper view of the wetting sensor 6. FIG. 5B is a sectional view of the wetting sensor 6 along an arrow V-V in FIG. 5A, FIG. 5B illustrating a section of the wetting sensor 6 viewed from the direction of the arrow V-V. Note that in FIG. 5A, a configuration below the water absorbing material 11 is indicated by a solid line.

In FIG. 5A, reference numerals "27a" to "27d" are each assigned to the multiple first electrodes connected to the first stretchable wiring line 25, such as a first electrode 27a to a first electrode 27d. Thus, the multiple first electrodes are distinguished from each other. Moreover, reference numerals "28a" to "28d" are each assigned to the multiple second electrodes connected to the second stretchable wiring line 26, such as a second electrode 28a to a second electrode 28d. Thus, the multiple second electrodes are distinguished from each other. The wetting sensor 6 is different from the wetting sensor 4 in connection of the electrodes with the second straight portion 25b and the fourth straight portion 26b.

Specifically, all electrodes positioned at locations of the first electrodes 27 connected to the second straight portion 25b of the wetting sensor 4 are the second electrodes 28c, 28d connected to the fourth straight portion 26b in the wetting sensor 6. Moreover, all electrodes positioned at locations of the second electrodes 28 connected to the fourth straight portion 26b of the wetting sensor 4 are the first electrodes 27c, 27d connected to the second straight portion 25b in the wetting sensor 6. That is, in the wetting sensor 6, a connection relationship of the first electrodes 27 and the second electrodes 28 to the second straight portion 25b and the fourth straight portion 26b is opposite to that in the wetting sensor 4.

In the wetting sensor 6, the first electrode 27a is positioned adjacent to the second electrode 28a in the Y-direction while being positioned adjacent to the second electrode 28c in an X-direction. Moreover, the second electrode 28a is positioned adjacent to the first electrode 27a and the first electrode 27b in the Y-direction while being positioned adjacent to the first electrode 27c in the X-direction. The first electrode 27b is positioned adjacent to the second electrode 28a and the second electrode 28b in the Y-direction while being positioned adjacent to the second electrode 28d in the X-direction. The second electrode 28b is positioned adjacent to the first electrode 27b in the Y-direction while being positioned adjacent to the first electrode 27d in the X-direction.

Moreover, in the wetting sensor 6, the second electrode 28c is positioned adjacent to the first electrode 27c in the Y-direction while being positioned adjacent to the first electrode 27a in the X-direction. The first electrode 27c is positioned adjacent to the second electrode 28c and the second electrode 28d in the Y-direction while being positioned adjacent to the second electrode 28a in the X-direction. The second electrode 28d is positioned adjacent to the first electrode 27c and the first electrode 27d in the Y-direction while being positioned adjacent to the first electrode 27b in the X-direction. The first electrode 27d is positioned adjacent to the second electrode 28d in the Y-direction while being positioned adjacent to the second electrode 28b in the X-direction.

As described above, in the wetting sensor 6, the first electrodes and the second electrodes are arranged adjacent to each other in the Y-direction and the X-direction. With this configuration, the wetting sensor 6 can detect, with high accuracy, any of leakage spreading in a lateral direction and leakage spreading in the longitudinal direction. Moreover, in the wetting sensor 6 and the wetting sensor 4, the second stretchable wiring line 26 is, without a "joint" such as an electrode or a contact, arranged as a continuous wiring line with the portions of the second stretchable wiring line 26 while sandwiching the first stretchable wiring line 25. Thus, stretchability of the second stretchable wiring line 26 does not locally vary at different regions of the second stretchable wiring line 26. Consequently, the second stretchable wiring line 26 may stretch uniformly.

Third Embodiment

Next, a third embodiment of the present disclosure will be described. The third embodiment is provided considering that stretching of a first stretchable wiring line and a second stretchable wiring line influences an impedance value. That is, when the first stretchable wiring line and the second stretchable wiring line stretch, the first stretchable wiring line and the second stretchable wiring line become longer. As a result, the sectional areas of the first stretchable wiring line and the second stretchable wiring line become smaller. In this case, an impedance between the first stretchable wiring line and the second stretchable wiring line is high regardless of wetness. Conversely, when the first stretchable wiring line and the second stretchable wiring line contract, the first stretchable wiring line and the second stretchable wiring line become shorter. As a result, the sectional areas of the first stretchable wiring line and the second stretchable wiring line become larger. In this case, the impedance between the first stretchable wiring line and the second stretchable wiring line is low regardless of wetness. Thus, a wetting sensor including wiring lines having stretchability shows that an impedance due to wiring line stretching overlaps with the measured impedance between the wiring lines. It can be said that in the wetting sensor including the wiring lines having the stretchability, the measured impedance between the wiring lines includes a change in the impedance due to wiring line stretching.

In view of the above-described point, reference wiring lines are provided together with stretchable wiring lines in the third embodiment. Thus, in the third embodiment, the influence of wiring line stretching on the impedance is eliminated or reduced by the reference wiring lines.

Figure 6A:
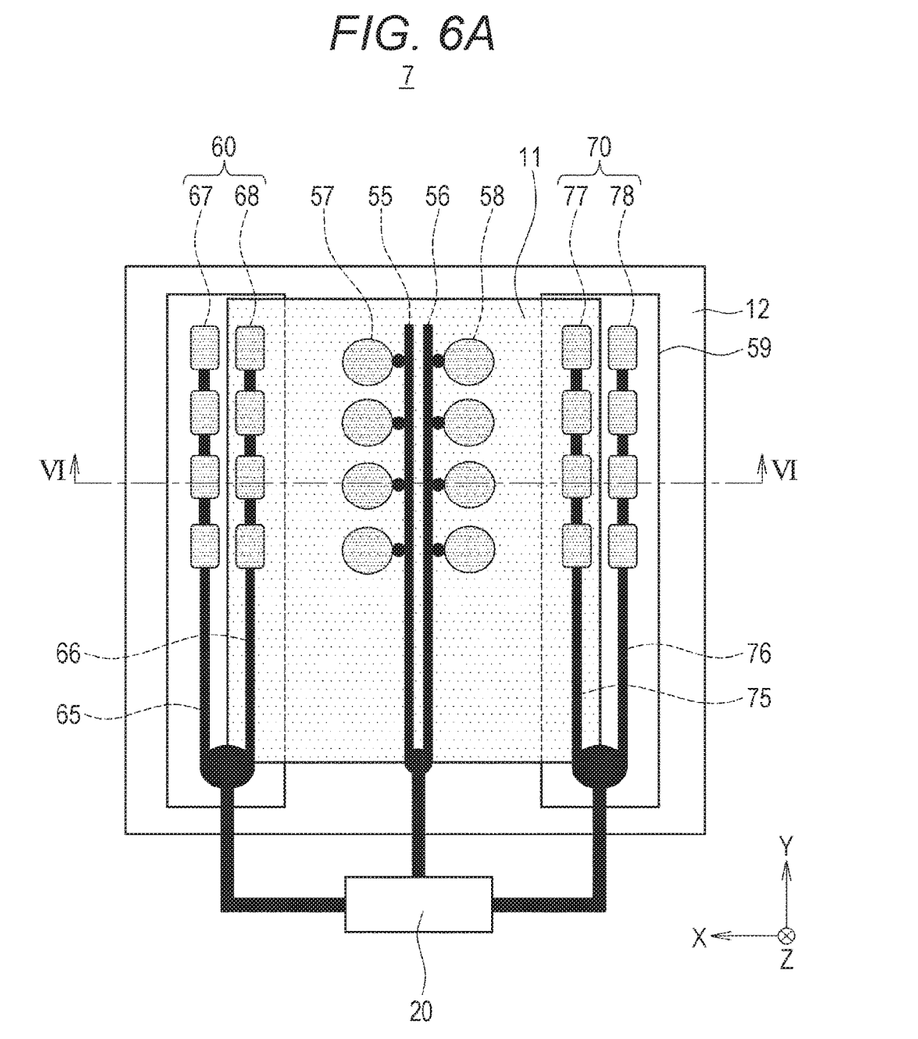
FIG. 6A is an upper view of a wetting sensor according to a third embodiment of the present disclosure.
Figure 6B:
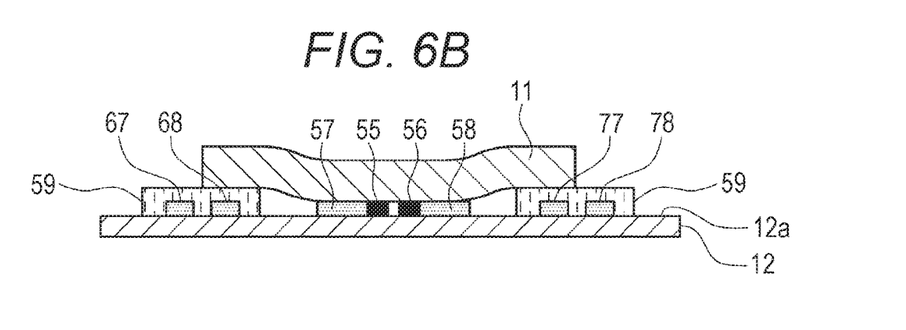
FIG. 6B is a sectional view of the wetting sensor according to the third embodiment of the present disclosure.

FIGS. 6A and 6B are views for describing a wetting sensor 7 according to the third embodiment. FIG. 6A is an upper view of the wetting sensor 7. FIG. 6B is a sectional view of the wetting sensor 7 along an arrow VI-VI in FIG. 6A, FIG. 6B illustrating a section of the wetting sensor 7 viewed from the direction of the arrow VI-VI. Note that in FIG. 6A, for the sake of convenience, a configuration below the water absorbing material 11 is indicated by a solid line.

The wetting sensor 7 has a first stretchable wiring line 55 and a second stretchable wiring line 56 formed on a stretchable circuit board 12, first electrodes 57 connected to the first stretchable wiring line 55, and second electrodes 58 connected to the second stretchable wiring line 56. The first electrodes 57 and the second electrodes 58 are covered with the water absorbing material 11. Further, the wetting sensor 7 according to the third embodiment has a measurer 20 configured to measure an impedance among the first electrodes 57 and the second electrodes 58.

Further, the wetting sensor 7 according to the third embodiment includes reference wiring lines 60, 70. The reference wiring line 60 includes reference wiring portions 65, 66 extending parallel to at least one of the first stretchable wiring line 55 and the second stretchable wiring line 56. The reference wiring line 70 includes reference wiring portions 75, 76 extending parallel to at least one of the first stretchable wiring line 55 and the second stretchable wiring line 56. At least a part of the reference wiring lines 60, 70 has a stretch ratio equal to that of at least one of the first stretchable wiring line 55 and the second stretchable wiring line 56.

In the third embodiment, all of the reference wiring portions 65, 66, 75, 76 are parallel to the first stretchable wiring line 55 and the second stretchable wiring line 56, and have the stretch ratio equal to those of the first stretchable wiring line 55 and the second stretchable wiring line 56.

Moreover, in the third embodiment, a material used for the reference wiring lines 60, 70 is the same as that of the first stretchable wiring line 55 and the second stretchable wiring line 56. Further, patterns of the reference wiring lines 60, 70 are formed such that the reference wiring lines 60, 70 have a width similar to those of the first stretchable wiring line 55 and the second stretchable wiring line 56. Further, in the third embodiment, a pattern 67 containing the same material as those of the first electrodes 57 and the second electrodes 58 is formed on the reference wiring portion 65, considering influence of the first electrodes 57 and the second electrodes 58 on stretching of the first stretchable wiring line 55 and the second stretchable wiring line 56. Similarly, a pattern 68 is formed on the reference wiring portion 66, a pattern 77 is formed on the reference wiring portion 75, and a pattern 78 is formed on the reference wiring portion 76.

According to the third embodiment, the reference wiring lines 60, 70 stretch as in the first stretchable wiring line 55 and the second stretchable wiring line 56. Thus, according to the third embodiment, the impedance of the reference wiring lines 60, 70 is measured, so that a change in the impedance due to wetting of the first stretchable wiring line 55 and the second stretchable wiring line 56 is measured while the influence of stretching of the first stretchable wiring line 55 and the second stretchable wiring line 56 can be eliminated or reduced.

In a disposable diaper 5, stress similar to that applied on the first stretchable wiring line 55 and the second stretchable wiring line 56 is applied on the reference wiring lines 60, 70. Thus, the reference wiring lines 60, 70 stretch substantially similarly to the first stretchable wiring line 55 and the second stretchable wiring line 56. For extracting, using the reference wiring line 60 and/or the reference wiring line 70, a change in the impedance due to wetting with the influence of wiring line stretching on the impedance being eliminated or reduced, the reference wiring line 60 and the reference wiring line 70 are kept dry. The wetting sensor 7 according to the third embodiment further includes a waterproof member 59 configured to prevent or reduce contact of the reference wiring lines 60, 70 with a water absorbing member. Thus, the reference wiring lines 60, 70 are kept dry. The waterproof member 59 is formed on the stretchable circuit board 12 while covering the reference wiring lines 60, 70.

Note that the third embodiment is not limited to the configuration including the reference wiring lines 60, 70 covered with the waterproof member 59. For example, in a case where the reference wiring lines 60, 70 can be arranged at such positions that the reference wiring lines 60, 70 are kept dry, the waterproof member 59 is not necessarily provided. Further, the third embodiment is not limited to the configuration in which two reference wiring lines 60, 70 are provided. At the wetting sensor 7, a single reference wiring line may be provided, or three or more reference wiring lines may be provided.

Figure 7:
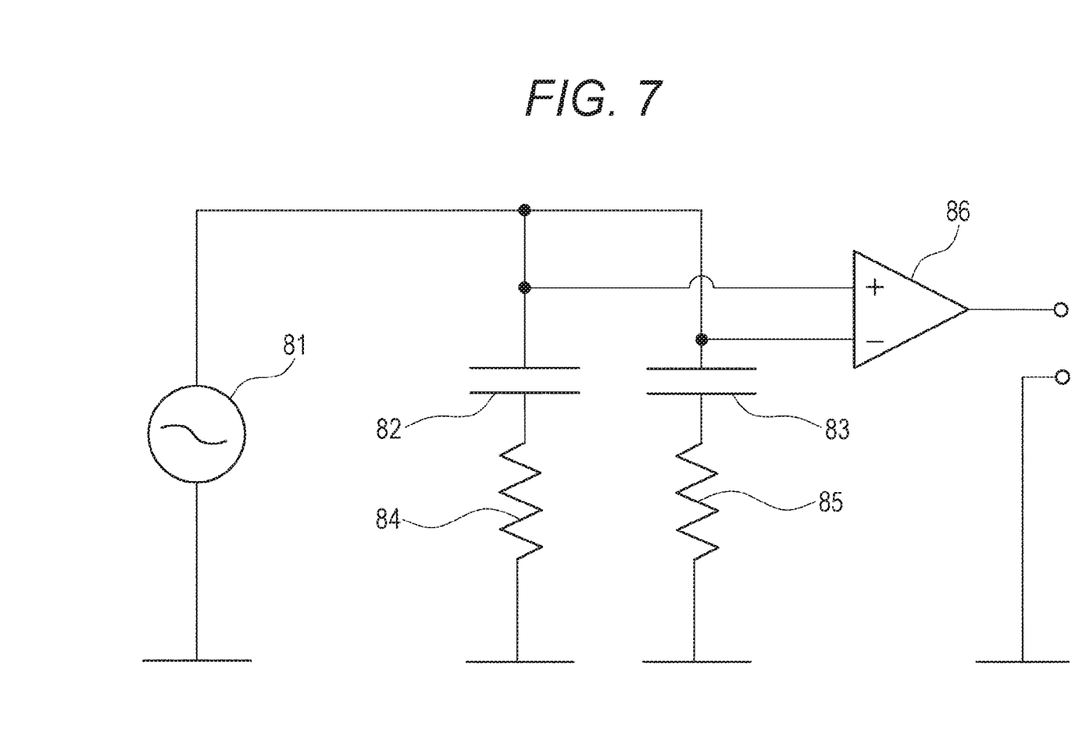
FIG. 7 is a diagram for describing a correction circuit according to the third embodiment of the present disclosure.

FIG. 7 is a diagram for describing a correction circuit. The correction circuit is configured to eliminate or reduce (hereinafter referred to as "correction of the impedance") a change in the impedance due to stretching of the first stretchable wiring line 55 and the second stretchable wiring line 56 from the impedance between the first stretchable wiring line 55 and the second stretchable wiring line 56. As illustrated in FIG. 6A, in the third embodiment, the reference wiring lines 60, 70 sandwich the first stretchable wiring line 55 and the second stretchable wiring line 56 while being formed in the direction of arrangement of the first stretchable wiring line 55 and the second stretchable wiring line 56. FIG. 7 illustrates the correction circuit configured to correct the impedance by using the reference wiring line 60 or the reference wiring line 70.

The correction circuit illustrated in FIG. 7 includes a power source 81, a sensor capacitor 82, a sensor internal resistor 84, a reference capacitor 83, a reference internal resistor 85, and a comparator 86. The electrostatic capacitance of the sensor capacitor 82 indicates the electrostatic capacitances of the first stretchable wiring line 55 and the second stretchable wiring line 56. The resistance value of the sensor internal resistor 84 indicates the internal resistances of the first stretchable wiring line 55 and the second stretchable wiring line 56. The sensor capacitor 82 and the sensor internal resistor 84 are connected in series. Any of the electrostatic capacitance of the sensor capacitor 82 and the resistance value of the sensor internal resistor 84 changes according to stretching of the first stretchable wiring line 55 and the second stretchable wiring line 56 and wetness of the first electrodes 57 and the second electrodes 58.

The electrostatic capacitance of the reference capacitor 83 indicates the electrostatic capacitances of the reference wiring portion 65 and the reference wiring portion 66. The resistance value of the reference internal resistor 85 indicates the internal resistances of the reference wiring portion 65 and the reference wiring portion 66. The reference capacitor 83 and the reference internal resistor 85 are connected in series. Any of the electrostatic capacitance of the reference capacitor 83 and the resistance value of the reference internal resistor 85 changes according to stretching of the reference wiring portion 65 and the reference wiring portion 66. Voltage supplied from the power source 81 is dropped by the sensor capacitor 82 and the sensor internal resistor 84. Moreover, the voltage supplied from the power source 81 is dropped by the reference capacitor 83 and the reference internal resistor 85. The voltage dropped by the sensor capacitor 82 and the sensor internal resistor 84 and the voltage dropped by the reference capacitor 83 and the reference internal resistor 85 are input to the comparator 86. The comparator 86 is configured to compare these two input voltages, and output a difference between these voltages. The output difference is a voltage value from which the influence of stretching of the first electrodes 57 and the second electrodes 58 is eliminated or reduced.

Note that in the present embodiment, the reference wiring line 60 (the reference wiring portion 65 and the reference wiring portion 66) is, by way of example, used for correction of the impedance. However, the reference wiring line 70 (the reference wiring portion 75 and the reference wiring portion 76) may be used instead of the reference wiring line 60 (the reference wiring portion 65 and the reference wiring portion 66). In the wetting sensor 7 of the third embodiment having the reference wiring lines 60, 70, each of the correction circuit including the reference wiring line 60 and the correction circuit including the reference wiring line 70 may correct the impedance between the first stretchable wiring line 55 and the second stretchable wiring line 56. Then, by, e.g., averaging of the impedances after correction, a final change in the impedance due to wetting may be calculated.

The above-described embodiments and examples include the following technical ideas.

A wetting sensor of <1> includes a stretchable circuit board having stretchability, first and second stretchable wiring lines as wiring lines formed on a main surface of the stretchable circuit board and having stretchability on the main surface, a first electrode connected to the first stretchable wiring line, a second electrode connected to the second stretchable wiring line, a water absorbing member configured to cover at least a part of each of the first electrode and the second electrode, and a measurer configured to measure electric characteristics between the first electrode and the second electrode which are contacting the water absorbing member.

A wetting sensor of <2> is the wetting sensor of <1>, in which the first electrode includes multiple first electrodes and the second electrode is positioned between adjacent ones of the multiple first electrodes.

A wetting sensor of <3> is the wetting sensor of <1> or <2>, in which the first stretchable wiring line has a first straight portion extending in one direction and a second straight portion extending parallel to the first straight portion, the first electrode is formed raised outward in a direction opposite to a direction from one of the first and second straight portions toward the other one of the first and second straight portions, the second stretchable wiring line has a third straight portion extending parallel to the first straight portion and a fourth straight portion extending parallel to the second straight portion, and some of the second electrodes are formed raised from the third straight portion toward the first straight portion and other of the second electrodes are formed raised from the fourth straight portion toward the second straight portion.

A wetting sensor of <4> is the wetting sensor of any one of <1> to <3>, which further includes a reference wiring line extending parallel to at least one of the first stretchable wiring line and the second stretchable wiring line. At least a part of the reference wiring line has a stretch ratio equal to that of at least one of the first stretchable wiring line and the second stretchable wiring line.

A wetting sensor of <5> is the wetting sensor of <4>, which further includes a waterproof member configured to prevent contact between the reference wiring line and the water absorbing member.

A wetting sensing system of <6> includes the wetting sensor of any one of <1> to <5> and a wetting determinator configured to determine a degree of water absorption of the water absorbing member based on the electric characteristics measured by the measurer of the wetting sensor.

The foregoing detailed description has been presented for the purposes of illustration and description. Many modifications and variations are possible in light of the above teaching. It is not intended to be exhaustive or to limit the subject matter described herein to the precise form disclosed. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims appended hereto.

What is claimed is:

1. A wetting sensor comprising:
   a stretchable circuit board having stretchability;
   a first stretchable wiring line as a wiring line formed on a surface of the stretchable circuit board and having stretchability in accordance with the stretchability of the stretchable circuit board;
   a second stretchable wiring line as a wiring line formed on the surface and having stretchability in accordance with the stretchability of the stretchable circuit board;
   a first electrode connected to the first stretchable wiring line;
   a second electrode connected to the second stretchable wiring line;
   a water absorbing member configured to cover at least a part of each of the first electrode and the second electrode; and
   a measurer configured to measure an electric characteristic between the first electrode and the second electrode which are contacting the water absorbing member,
   wherein the first electrode includes multiple first electrode elements and the second electrode includes multiple second electrode elements.

2. The wetting sensor according to claim 1, wherein each of the second electrode elements is positioned between adjacent ones of the multiple first electrode elements.

3. A wetting sensor comprising:
   a stretchable circuit board having stretchability;
   a first stretchable wiring line as a wiring line formed on a surface of the stretchable circuit board and having stretchability in accordance with the stretchability of the stretchable circuit board;

a second stretchable wiring line as a wiring line formed on the surface and having stretchability in accordance with the stretchability of the stretchable circuit board;
a first electrode connected to the first stretchable wiring line;
a second electrode connected to the second stretchable wiring line;
a water absorbing member configured to cover at least a part of each of the first electrode and the second electrode; and
a measurer configured to measure an electric characteristic between the first electrode and the second electrode which are contacting the water absorbing member, wherein:
the first stretchable wiring line has
a first straight portion extending in one direction; and
a second straight portion extending parallel to the first straight portion,
the first electrode is formed raised in a direction opposite to a direction from the first straight portion toward the second straight portion or in a direction opposite to a direction from the second straight portion toward the first straight portion,
the second stretchable wiring line has
a third straight portion extending parallel to the first straight portion, and
a fourth straight portion extending parallel to the second straight portion, and
the second electrode includes multiple second electrodes, and
some of the second electrodes are formed raised from the third straight portion toward the first straight portion, and other of the second electrodes are formed raised from the fourth straight portion toward the second straight portion.

4. The wetting sensor according to claim 1, further comprising:
a reference wiring line extending parallel to at least one of the first stretchable wiring line and the second stretchable wiring line, wherein
at least a part of the reference wiring line has a stretch ratio equal to that of at least one of the first stretchable wiring line and the second stretchable wiring line.

5. A wetting sensor comprising:
a stretchable circuit board having stretchability;
a first stretchable wiring line as a wiring line formed on a surface of the stretchable circuit board and having stretchability in accordance with the stretchability of the stretchable circuit board;
a second stretchable wiring line as a wiring line formed on the surface and having stretchability in accordance with the stretchability of the stretchable circuit board;
a first electrode connected to the first stretchable wiring line;
a second electrode connected to the second stretchable wiring line;
a water absorbing member configured to cover at least a part of each of the first electrode and the second electrode;
a measurer configured to measure an electric characteristic between the first electrode and the second electrode which are contacting the water absorbing member,
a reference wiring line extending parallel to at least one of the first stretchable wiring line and the second stretchable wiring line, and
a waterproof member configured to prevent or reduce contact between the reference wiring line and the water absorbing member,
wherein at least a part of the reference wiring line has a stretch ratio equal to that of at least one of the first stretchable wiring line and the second stretchable wiring line.

6. A wetting sensing system comprising:
the wetting sensor according to claim 1; and
a wetting determinator configured to determine a degree of water absorption of the water absorbing member based on the electric characteristic measured by the measurer of the wetting sensor.

7. The wetting sensor according to claim 1, wherein the electric characteristic comprises impedance.

8. The setting sensing system according to claim 6, wherein the wetting determinator comprises a processor for determining wetting.

* * * * *